United States Patent [19]

Eckstein et al.

[11] Patent Number: 4,897,223
[45] Date of Patent: Jan. 30, 1990

[54] TRI-PHENYL METHYL COLOR-FORMING AGENTS

[75] Inventors: Udo Eckstein, Cologne; Hubertus Psaar; Roderich Raue, both of Leverkusen, all of Fed. Rep. of Germany

[73] Assignee: Bayer Aktiengesellschaft, Leverkusen, Fed. Rep. of Germany

[21] Appl. No.: 162,531

[22] Filed: Mar. 1, 1988

[30] Foreign Application Priority Data

Mar. 10, 1987 [DE] Fed. Rep. of Germany ....... 3707548

[51] Int. Cl.$^4$ ........................................... C07C 121/80
[52] U.S. Cl. ...................................... 544/73; 260/386; 260/388; 544/73; 544/74; 544/86; 544/162; 544/163; 544/169; 544/253; 546/94; 546/166; 546/229; 546/230; 546/232; 546/234; 546/235; 548/217; 548/373; 548/440; 548/490; 548/563; 548/577; 552/105; 552/108; 552/109; 552/110
[58] Field of Search ...................... 260/385, 388, 390; 544/73, 74, 86, 162, 163, 169, 253; 546/94, 166, 229, 230, 232, 234, 235; 548/217, 373, 440, 490, 563, 577

[56] References Cited

U.S. PATENT DOCUMENTS 4,783,196  11/1988  Eckstein et al. .................... 260/390

OTHER PUBLICATIONS

Aoyama et al., Chemical Abstracts, vol. 104 (1986), 30931n.
Aoyama et al., Chemical Abstracts, vol. (1986), 126,149a.

Primary Examiner—Richard L. Raymond
Attorney, Agent, or Firm—Sprung, Horn, Kramer & Woods

[57] ABSTRACT

Color-forming agents of the general formula

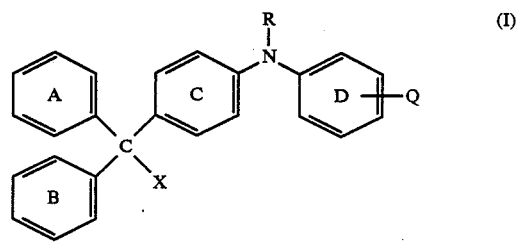

(I)

wherein

X denotes hydroxyl, alkoxy, alkenyloxy, aralkoxy, cycloalkoxy, aryloxy, acyloxy, alkoxycarbonyloxy, alkylamino, dialkylamino, acylamino, aralkylamino or arylamino, Q denotes cyano, alkoxycarbonyl, aryloxycarbonyl, aralkoxycarbonyl, carbamoyl, N-alkylcarbamoyl, N,N-dialkylcarbamoyl, N-alkyl-N-aryl-carbamoyl, acyl, alkoxysulphonyl, aralkoxysulphonyl, sulphamoyl, N-alkylsulphamoyl, N,N-dialkylsulphamoyl, alkylsulphonyl, arylsulphonyl or aralkylsulphonyl and R denotes alkyl, alkenyl or aralkyl, further isocyclic or heterocyclic rings can be fused on to the rings A, B, C and D, and the cyclic and acyclic radicals and the rings A, B, C and D can carry further substituents, are used for the preparation of pressure-sensitive recording materials.

2 Claims, No Drawings

TRI-PHENYL METHYL COLOR-FORMING AGENTS

The invention relates to colour-forming agents of the general formula

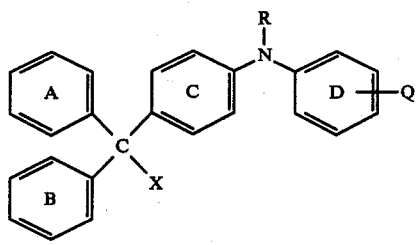

wherein
X denotes hydroxyl, alkoxy, alkenyloxy, aralkoxy, cycloalkoxy, aryloxy, acyloxy, alkoxycarbonyloxy, alkylamino, dialkylamino, acylamino, aralkylamino, or arylamino,
Q denotes cyano, alkoxycarbonyl, aryloxycarbonyl, aralkoxycarbonyl, carbamoyl, N-alkylcarbamoyl, N,N-dialkylcarbamoyl, N-alkyl-N-aryl-carbamoyl, acyl, alkoxysulphonyl, aralkoxysulphonyl, sulphamoyl, N-alkylsulphamoyl, N,N-dialkylsulphamoyl, alkylsulphonyl, arylsulphonyl or aralkylsulphonyl and
R denotes alkyl, alkenyl or aralkyl,
further isocyclic or heterocyclic rings can be fused on to the rings A, B, C and D, and the cyclic and acyclic radicals and the rings A, B, C and D can carry further non-ionic substituents which are customary in dyestuffs chemistry, or mixtures thereof, their preparation and their use for the preparation of pressure-sensitive recording materials.

Nonionic substituents which are customary in dyestuffs chemistry are, for example, halogen, hydroxyl, alkoxy, alkenyloxy, aryloxy, aralkoxy, cycloalkyloxy, heteryloxy, aryl, heteryl, alkylmercapto, arylmercapto, aralkylmercapto, alkylsulphonyl, cyano, carbamoyl, alkoxycarbonyl, amino, which can be substituted by 1 or 2 alkyl, cycloalkyl, aryl or aralkyl groups, preferably to form a 5- or 6-membered ring, or the substituents of which can be cyclized, acylamino, alkenyloxy, alkylcarbonyloxy and arylcarbonyloxy, and, as substituents of the rings, also alkyl, aryl, aralkyl, alkenyl or arylvinyl.

Alkyl represents $C_1$–$C_{30}$-alkyl, in particular $C_1$–$C_{12}$-alkyl.

The alkyl radicals and the alkyl radicals in alkoxy, alkylthio, alkylamino, alkanoylamino, alkylsulphonyl and alkoxycarbonyl groups can be branched and substituted, for example, by fluorine, chlorine, $C_1$- to $C_4$-alkoxy, cyano or $C_1$-$C_4$-alkoxycarbonyl.

Aralkyl is, in particular, phenyl-$C_1$- to -$C_4$-alkyl, which can be substituted in the phenyl nucleus by halogen, $C_1$- to $C_4$-alkyl and/or $C_1$- to $C_4$-alkoxy.

Cycloalkyl is, in particular, cyclopentyl or cyclohexyl which is optionally substituted by methyl.

Alkenyl is, in particular, $C_2$–$C_5$-alkenyl, which can be monosubstituted by hydroxyl, $C_1$- to $C_4$-alkoxy, cyano, $C_1$- to $C_4$-alkoxycarbonyl, chlorine or bromine. Vinyl and allyl are preferred.

Halogen is, in particular, fluorine, chlorine and bromine, preferably chlorine.

Aryl is, in particular, phenyl or naphthyl which is optionally substituted by one to three substituents from the group comprising $C_1$- to $C_4$-alkyl, chlorine, bromine, cyano, $C_1$- to $C_4$-alkoxycarbonyl and $C_1$- to $C_4$-alkoxy.

Alkoxy is, in particular, $C_1$–$C_{12}$-alkoxy which is optionally substituted by chlorine or $C_1$–$C_4$-alkoxy.

Acyl is, in particular, $C_1$- to $C_4$-alkylcarbonyl or benzoyl.

Alkoxycarbonyl is, in particular, $C_1$- to $C_4$-alkoxycarbonyl which is optionally substituted by hydroxyl, halogen or cyano.

Heteryl is, in particular, pyridyl, pyrimidyl, pyrazinyl, triazinyl, indolyl, imidazolyl, oxazolyl, thiazolyl, triazolyl, thiadiazolyl or tetrazolyl, which can be benzofused, and their partly hydrogenated or completely hydrogenated derivatives.

Preferred non-ionic substituents of the rings are $C_1$–$C_4$-alkyl, $C_1$–$C_4$-alkoxy, cyano and halogen.

Of the colour-forming agents of the formula I, those which are of particular importance are the compounds of the formula

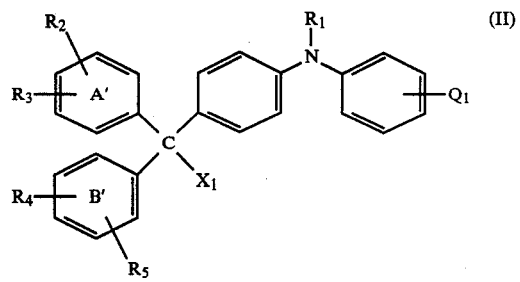

wherein
$X_1$ denotes hydroxyl; $C_1$–$C_{12}$-alkoxy which is optionally substituted by chlorine or $C_1$–$C_4$-alkoxy; $C_2$–$C_{12}$-alkenyloxy; or benzyloxy or phenylethyloxy which is optionally substituted by $C_1$–$C_4$-alkyl, $C_1$–$C_4$-alkoxy or halogen,
$Q_1$ denotes cyano; $C_1$–$C_{12}$-alkoxycarbonyl; benzyloxycarbonyl; N,N-di-$C_1$–$C_4$-alkylcarbamoyl or $C_1$–$C_4$-alkylcarbonyl which is optionally substituted by chlorine or $C_1$–$C_4$-alkoxy; $C_1$–$C_{12}$-alkoxysulphonyl which is optionally substituted by chlorine or $C_1$–$C_4$-alkoxy, $C_1$–$C_{12}$-alkylsulphonyl or benzylsulphonyl which is optionally substituted by chlorine, $C_1$–$C_4$-alkyl or $C_1$–$C_4$-alkoxy,
$R_1$ denotes $C_1$–$C_{12}$-alkyl or benzyl,
$R_2$ and $R_4$ independently of one another denote hydrogen, chlorine, $C_1$–$C_{12}$-alkyl, $C_1$–$C_{12}$-alkoxy, phenoxy, benzyloxy or a radical of the formula

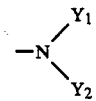

$R_3$ and $R_5$ independently of one another denote hydrogen; chlorine, $C_1$–$C_{12}$-alkyl; $C_2$–$C_{12}$-alkenyl; $C_1$–$C_{12}$-alkoxy; $C_2$–$C_{12}$-alkenyloxy; phenyl, benzyl, phenoxy or benzyloxy; which is optionally substituted by chlorine, $C_1$–$C_{12}$-alkyl or $C_1$–$C_{12}$-alkoxy; cyclohexyloxy or cyclopentyloxy which is optionally substituted by $C_1$–$C_{12}$-alkyl; $C_1$–$C_{12}$-alkylmercapto or a radical of the formula

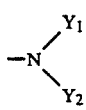

$Y_1$ and $Y_2$ independently of one another denote $C_1$–$C_{12}$-alkyl which is optionally substituted by chlorine, cyano, $C_1$–$C_4$-alkoxycarbonyl or $C_1$–$C_4$-alkoxy; or cyclohexyl, phenyl or benzyl, which can be substituted by chlorine, $C_1$–$C_{12}$-alkyl or $C_1$–$C_{12}$-alkoxy, or $R_2$ and $R_3$ denote members which, together with ring A' and/or $R_4$ and $R_5$ denote members which, together with ring B', are necessary to complete a ring system of the following formulae

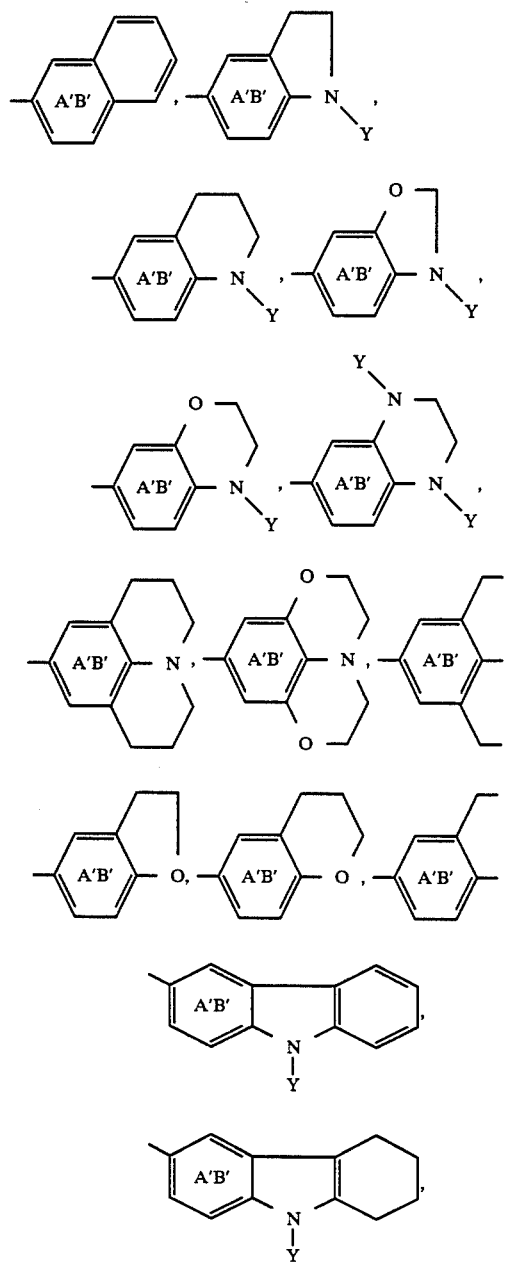

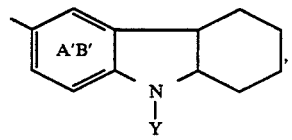

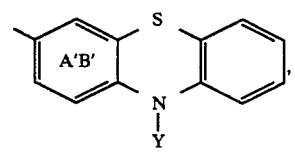

wherein Y represents $C_1$–$C_{12}$-alkyl, which can be substituted by chlorine, cyano, $C_1$–$C_4$-alkoxycarbonyl or $C_1$–$C_4$-alkoxy; or cyclohexyl, phenyl or benzyl, which can be substituted by chlorine, $C_1$–$C_{12}$-alkyl with $C_1$–$C_{12}$-alkoxy, and the saturated ring component can carry up to 4 radicals from the group comprising chlorine, $C_1$- to $C_4$-alkyl, $C_1$- to $C_4$-alkoxy and phenyl, or

denotes a pyrrolo, pyrrolidino, piperidino, pipecolino, morpholino, pyrazolo or pyrazolino radical which is optionally substituted by chlorine, $C_1$- to $C_4$-alkyl or phenyl.

Examples of radicals which are substituted in the saturated ring are:

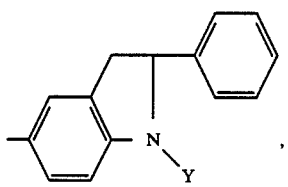

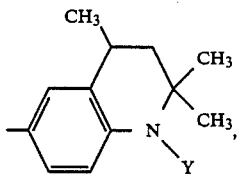

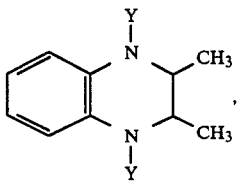

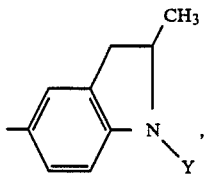

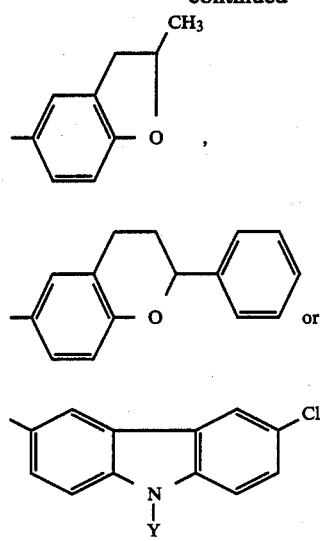

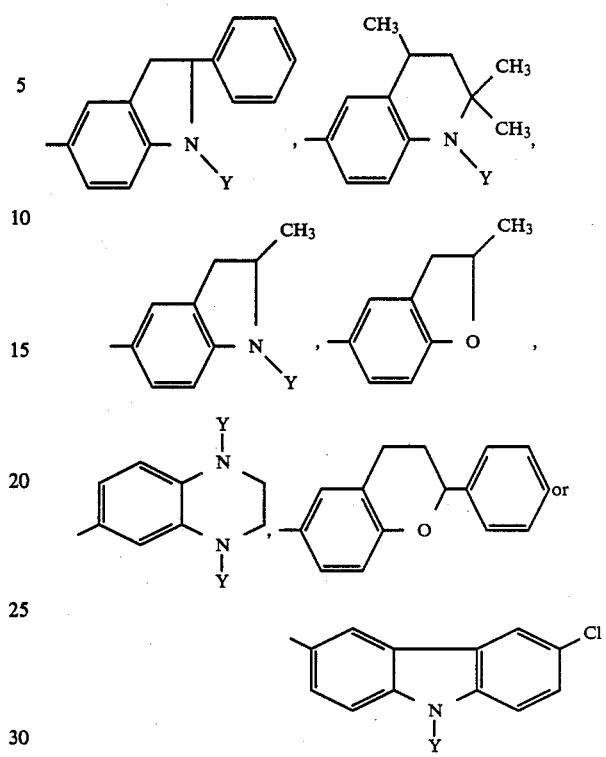

and $R_1$, Y, $Y_1$ and $Y_2$ have the abovementioned meaning.

The colour-forming agents of the formula 1 can be prepared by processes which are known per se. One process comprises, for example, a procedure in which dyestuffs salts of the formula Particularly preferred colour-forming agents are those of the formula

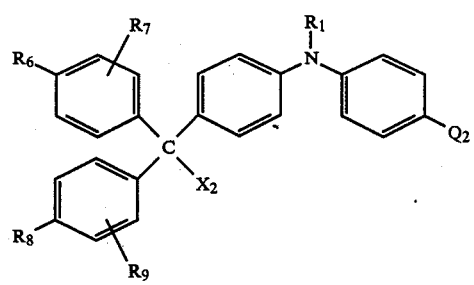

(III)

wherein $X_2$ denotes hydroxyl or $C_1$–$C_{12}$-alkoxy, $Q_2$ denotes cyano, $C_1$–$C_{12}$-alkoxycarbonyl or $C_1$–$C_4$-alkylcarbonyl, $R_6$ denotes hydrogen, chlorine, $C_1$–$C_{12}$-alkyl, $C_1$–$C_{12}$-alkoxy, benzyloxy or a radical of the formula

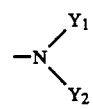

$R_8$ denotes $C_1$–$C_{12}$-alkoxy, benzyloxy or a radical of the formula

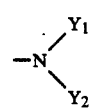

$R_7$ and $R_9$, independently of one another, denote hydrogen, chlorine, $C_1$–$C_{12}$-alkyl, $C_1$–$C_{12}$-alkoxy, $C_1$–$C_4$-alkylamino or di-$C_1$–$C_{12}$-alkylamino, or $R_6$ and $R_8$ denote members which, together with the benzene ring to which they are bonded, are required to complete a ring system of the formulae

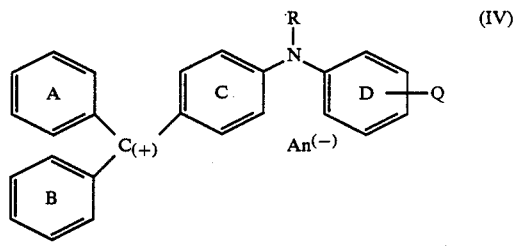

(IV)

are reacted with bases of the formula

Mex (V)

wherein

R, X, Q and the rings A, B, C and D have the abovementioned meaning,

Me denotes an alkali metal or alkaline earth metal, in particular sodium or potassium and $An^{(-)}$ denotes an anion from the series comprising chloride, bromide, acetate, sulphate, phosphate or

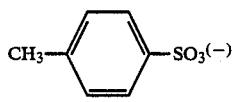

in an organic solvent suitable for the reaction. After removal of the solvent if necessary, the mixture is then poured onto water and the compounds of the formula I are isolated.

Polar solvents, such as dimethylformamide, dimethyl sulphoxide, hexamethyl-phosphoric acid triamide and alkanols, are a suitable reaction medium. Dimethylformamide and $C_1$–$C_8$-alkanols are preferred.

Suitable reaction temperatures lie between 20° and 120° C., and 30° to 80° C. are preferred.

A particularly advantageous preparation process comprises a procedure in which ketones of the formula

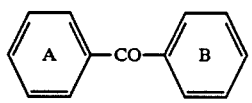

VI are subjected to a condensation reaction with amines of the formula

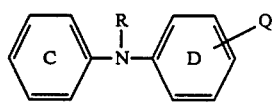

VII or ketones of the formula

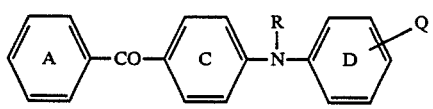

VIII are subjected to a condensation reaction with compounds of the formula

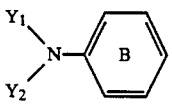

IX in a one-pot reaction in the presence of a condensing agent which supplies an anion $An^{(-)}$, to give the colour salts of the formula (IV), and these are reacted with the bases (V) as described above, without intermediate isolation.

Phosphorus oxychloride and/or diphosphorus pentoxide are preferably used here as condensing agents.

The colour-forming agents of the formula I obtained can be marketed without further purification and can be used in pressure-sensitive recording material, in particular in microencapsulated materials.

The colour-forming agents of the formula I according to the invention are usually colourless or at most slightly coloured and have a very high solubility in the (chloro)hydrocarbons customary for encapsulation.

On contact with an acid developer, that is to say an electron acceptor, they give intense blue, green-blue, green, violet or red colour shades, which are excellently fast to sublimation and light. Navy blue, grey or black colorations can be achieved by mixtures with one another.

They are also useful when mixed with one or more other known colour-forming agents, for example 3,3-bis-(aminophenyl)-phthalides, 3,3-bis-(indolyl)-phthalides, 3-amino-fluoranes, 2,6-diamino-fluoranes, leukoauramines, spiropyrans, spirodipyrans, chromenoindoles, phenoxazines, phenothiazines, carbazolyl-methanes or other triarylmethane leuko dyestuffs, to give green, violet, blue, navy blue, grey or black colorations.

They exhibit a high colour intensity, outstanding fastness to light and excellent ageing- and CB stability both on phenolic substrates and on salicylate and activated clays. They are suitable for pressure-sensitive recording material which can be used either as copying or as registering material. Their speed of development varies according to the substituents. However, they are in general distinguished by a high speed of development coupled with a reduced sensitivity of the recording materials to unintentional premature development.

By substitution with long-chain alkyl radicals, the solubility of the colour-forming agents is increased so that highly concentrated solutions in the solvents suitable for microencapsulation can be prepared.

Pressure-sensitive recording materials are known, for example, from U.S. patent specification Nos. 2,800,457 and 2,800,458.

EXAMPLE 1

13.5 g (0.05 mol) of 4,4'-diethoxybenzophenone and 10.4 g (0.05 mol) of N-methyl-N-phenyl-4-cyanophenylamine are suspended in 38.2 g (0.25 mol) of phosphorus oxychloride, and 14.1 g (0.1 mol) of phosphorus pentoxide are added at room temperature. The mixture is stirred at 40° C. for 20 hours. It is poured onto 500 ml of ice-water and stirred at room temperature for about 10–15 hours until the dyestuff separates out as crystals. Filtration with suction, washing with water and drying in vacuo at 40° C. gives 24.1 g (97% of theory) of dark red-violet crystals of melting point: 69°–75° C.

A solution of 19.9 g (0.04 mol) of this dyestuff in 200 ml of ethanol is slowly added dropwise to 120 ml (0.12 mol) of an initial 1 molar sodium ethylate solution at room temperature. The mixture is stirred at room temperature for 20 hours, the salt which has precipitated out is filtered off and the solvent is removed. The oily residue which remains is stirred into 500 ml of water and the mixture is cooled to about 10° to 15° C. and filtered. After drying in vacuo at room temperature, 18.5 g (91% of theory) of an almost colourless crystalline powder of melting point: 48°–55° C. and the formula

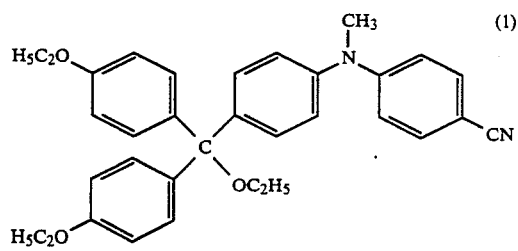

(1)

are obtained.

A solution in glacial acetic acid becomes dark-violet with $\lambda_{max}=554$ nm and $\lambda_2=442$ nm IR spectrum (KBr disc): 2210 $cm^{-1}$—CN);

$^1$H NMR spectrum ($CDCl_3$): $\delta=1.22$ ppm (T, 3H), $\delta=1.3$ ppm (T, 6H), $\delta=3.1$ ppm (Q, 2H), $\delta=3.3$ ppm (S, 3H), $\delta=4$ ppm (Q, 4H)

Mass spectrum: $C_{33}H_{34}N_2O_3$ (506.7), m/e 506 (12%) $M^+$, m/e 461 (100%) $M\pm OC_2H_5$ A strong reddish grey-black colour shade is developed on acid clay.

EXAMPLE 2

If the procedure is as described in the above example, but 14.3 g (0.05 mol) of 4-methoxy-4'-methoxy-ethoxybenzophenone are used instead of 4,4'-diethoxybenzophenone and sodium isopropylate/isopropanol is used instead of sodium ethylate/ethanol, 19.5 g (72% of theory) of beige crystals of the formula

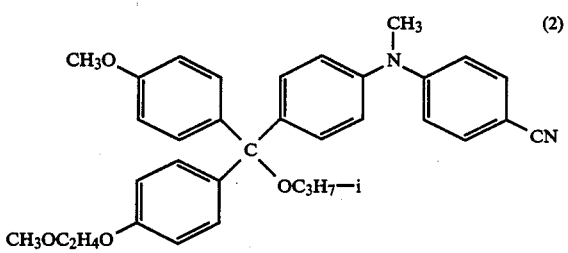

(2)

which give a grey-black colour shade on acid clay and phenolic resin, are obtained.

Absorption in glacial acid $\lambda_{max}=556$ nm and $\lambda_2=440$ nm.

EXAMPLE 3

If, as described in Example 1, 13.6 g (0.05 mol) of 2,4,4'-trimethoxybenzophenone are used instead of 13.5 g of 4,4'-diethoxybenzophenone in the preparation of the dyestuff, the reaction gives 23 g (92.4% of theory) of the corresponding dyestuff in the form of red-brown crystals with a metallic gloss.

10 g (0.02 mol) of this dyestuff are dissolved in 100 ml of dimethylformamide, and 10 g of 20% strength sodium hydroxide solution are slowly added at room temperature. After the reaction mixture has been stirred for 2 hours, it is poured onto 1 l of ice-water. After addition of 50 g of sodium chloride, the colourless crystalline precipitate is filtered off with suction. Drying in vacuo at 40° C. gives 8.8 g (91.7% of theory) of colourless crystals of melting point: 68°-80° C. and the formula

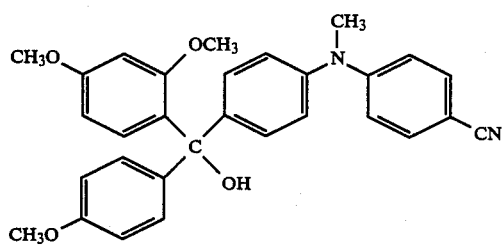

(3)

which can be recrystallized from isopropanol. Melting point: 78°-81° C. In glacial acetic acid, a dark blue-violet colour shade is developed with $\lambda_{max}=566$ nm and $\lambda_2=476$ nm. The IR spectrum shows the characteristic CN band at 2205 cm$^{-1}$ and the $^1$H NMR spectrum shows the following signals: $\delta=5.1$ ppm (S, 1H) $\delta=3.33$ (S, 3H) $\delta=3.67$ ppm (S, 3H), $\delta=3.79$ (S, 3H) and $\delta=3.81$ (S, 3H).

Mass spectrum: $C_{30}H_{28}N_2O_4$ (480.6) m/e 480 (27%) M$^+$, m/e 463 (15%) M$^+$—OH.

A blue-violet colour shade with outstanding CF- and CB-stabilities is obtained on acid clay or bisphenol A.

EXAMPLE 4

11.4 g (0.04 mol) of 4-ethoxy-4'-ethylmercaptobenzophenone and 11.4 g of phosphorus pentoxide are added in succession to a solution of 8.32 g (0.04 mol) of N-methyl-N-phenyl-4-cyanophenylamine in 30.6 g of phosphorus oxychloride at room temperature. The reaction mixture is warmed to 40° C. and is stirred at this temperature for 16 hours. The melt is cooled to 20° C. and then dissolved in 150 ml of dimethylformamide, with cooling. 24 g (0.12 mol) of 20% strength sodium hydroxide solution are added dropwise, with vigourous stirring, such that a temperature of 40° C. is established. The mixture is subsequently stirred at 40° C. for a further hour, the salt is filtered off and the solution is poured onto 500 ml of ice-water. After addition of 25 g of sodium chloride, the colourless crystalline precipitate is filtered off with suction and washed with 1% strength sodium hydroxide solution and water. Drying in vacuo gives 14.3 g (72.4% of theory) of the colour-forming agent of the formula

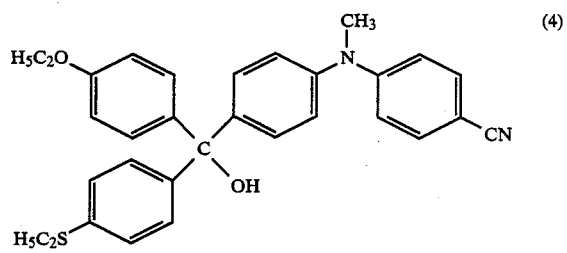

(4)

with the melting range: 59°-70° C. A solution in glacial acetic acid is blue with $\lambda_{max}=576$ nm and $\lambda_2=480$ nm. The IR spectrum shows the characteristic CN band at 2221 cm$^{-1}$ and the mass spectrum gives m/e 494 (48%) M$^+$ and m/e 478 (16%) M$^+$—OH. ($C_{31}H_{30}N_2SO_2$ (404.7).

A very stable blue is obtained on acid clay.

EXAMPLE 5

The following colour-forming agents are also prepared analogously to Example 1–4.

TABLE 1

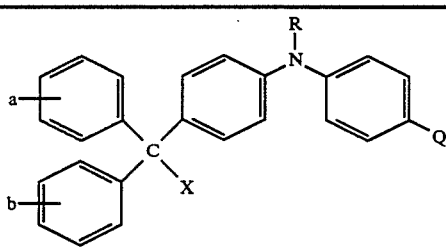

| Formula No. | a | b | R | Q | X | Colour shade on acid clay or bisphenol A |
|---|---|---|---|---|---|---|
| 5 | 4-OCH$_3$ | 4-OCH$_3$ | CH$_3$ | CN | OC$_4$H$_9$—n | black-grey |
| 6 | 4-OCH$_3$ | 4-OCH$_3$ | CH$_2$—C$_6$H$_5$ | CN | OC$_2$H$_5$ | black-grey |
| 7 | 4-OCH$_3$ | 3-OCH$_3$ 4-OCH$_3$ | CH$_3$ | CN | OCH$_3$ | grey-blue |
| 8 | 3-OCH$_3$ | 3-OCH$_3$ 4-OCH$_3$ | C$_2$H$_5$ | CN | OC$_2$H$_5$ | blue |
| 9 | 4-OCH$_3$ | 3-CH$_3$ 4-SCH$_3$ | CH$_3$ | CN | OH | dark red-violet |
| 10 | 4-OCH$_3$ | 2-OCH$_3$ 3-OCH$_3$ 4-OCH$_3$ | CH$_3$ | CN | OC$_3$H$_7$—i | violet |
| 11 | 4-OCH$_3$ | 3-C$_3$H$_7$—i 4-OCH$_3$ 3-C$_3$H$_7$—i | CH$_3$ | CN | OC$_3$H$_7$—i | blue-black |
| 12 | 4-OC$_2$H$_5$ | 4-OC$_2$H$_5$ | CH$_3$ | CO—CH$_3$ | OC$_2$H$_5$ | grey-black |
| 13 | 2-CH$_3$ 4-OCH$_3$ | 3-OCH$_3$ | CH$_2$—C$_6$H$_5$ | COOCH$_3$ | OCH$_3$ | red |
| 14 | 2-Cl 4-OC$_3$H$_7$ | 3-OCH$_3$ 4-OCH$_3$ | CH$_3$ | COOC$_2$H$_5$ | OC$_6$H$_{13}$ | dark red-violet |
| 15 | 4-C$_{12}$H$_{25}$ | 2-OCH$_3$ 4-OCH$_3$ | C$_4$H$_9$ | CN | OC$_4$H$_9$ | dark red |

EXAMPLE 6

13.6 g (0.04 mol) of 2,4'-diethoxy-4-diethylaminobenzophenone and 8.3 g (0.04 mol) of N-methyl-N-phenyl-4-cyanophenylamine are suspended in 30.6 g (0.2 mol) of phosphorus oxychloride, and 11.3 g (0.08 mol) of phosphorus pentoxide are slowly added. The reaction mixture is stirred at 40° C. for 20 hours. The melt is then poured onto 600 ml of ice-water, the mixture is stirred for 10 hours and the precipitate, which is then crystalline, is filtered off with suction. Drying in vacuo at 40° C. gives 18.8 g (82.8% of theory) of a brownish crystalline powder.

17 g (0.03 mol) of this dyestuff are dissolved in 70 ml of dimethylformamide and the solution is filtered. 15 g of 20% strength sodium hydroxide solution are added dropwise to the solution in the course of 1 hour. The mixture is stirred at 40° C. for 2 hours and filtered and the solution is introduced into 500 ml of ice-water. After addition of 40 g of sodium chloride, the mixture is briefly stirred and filtered with suction. The filter cake is then suspended in 50 ml of methanol and is filtered off again with suction. Drying in vacuo gives 9.5 g (57.6% of theory) of a pale grey crystalline powder of melting point: 147°-54° C. of the formula

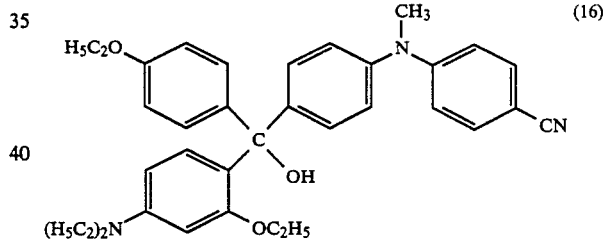

which dissolves in glacial acetic acid and gives a blue colour with $\lambda_{max}=604$ nm and $\lambda_2=477$ nm.

A deep dark-blue coloration with excellent fastness to light and stability to ageing is obtained on acid clay.

EXAMPLE 7

14.4 g (0.05 mol) of 4-(N-methyl-N-phenylamino)benzophenone and 10.4 g (0.05 mol) of N-methyl-N-phenyl-4-cyanophenylamine are suspended in 38.2 g of phosphorus oxychloride, and 14.1 g of phorphorus pentoxide are added at room temperature. The mixture is stirred at 40° C. for 20 hours and dissolved in 250 ml of methanol, with external cooling, so that the temperature does not rise above 50° C. 24 g (0.12 mol) of 20% strength sodium hydroxide solution are added dropwise, with thorough stirring, the temperature remaining between 40° and 50° C. The dropwise addition time is 1 hour. The mixture is stirred at 40°-50° C. for 5 hours, and 250 ml of water are added. It is cooled to 10°-15° C. and the almost colourless precipitate is filtered off with suction. Washing with methanol/water and drying gives 18.3 g (73.8% of theory) of almost colourless crystals of melting range: 55°-61° C. and a formula consisting of a mixture of the carbinol base methyl ether (about 80%) and the carbinol base (about 20%) of the formula

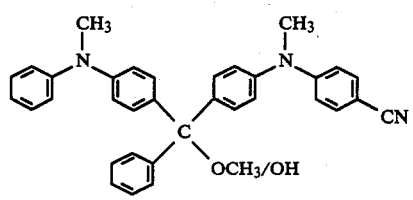

(17)

Absorption in glacial acetic acid: $\lambda_{max}=626$ nm; $\lambda_2=437$ nm.

The colour-forming agent develops a deep green colour shade with good fastness properties on acid clay and phenolic resin.

EXAMPLE 8

The following colour-forming agents in Table 2 are obtained in the same manner as described in Example 6 and 7.

TABLE 2

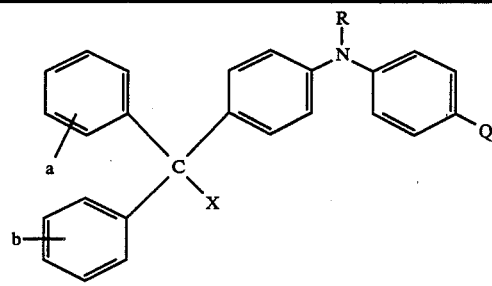

| Formula No. | a | b | R | Q | X | Colour shade on acid clay or bisphenol A |
|---|---|---|---|---|---|---|
| 18 | 4-OCH₃ | 4-N(CH₃)₂ | C₄H₉ | CN | OCH₃ | grey-blue |
| 19 | 4-OC₂H₅ | 2-CH₃<br>4-N(C₂H₅)₂ | CH₃ | CN | OCH₃ | blue |
| 20 | 2-OCH₃ | 4-N—C₂H₅<br>\|<br>CH₂—C₆H₅ | CH₃ | CN | OC₆H₁₃ | green |
| 21 | 4-OCH₃ | 2-CH₃<br>4-N—C₂H₅<br>\|<br>C₂H₄—Cl | CH₃ | CN | OH | blue |
| 22 | 2-Cl<br>4-Cl | 4-N—C₂H₅<br>\|<br>C₂H₄—CN | C₂H₅ | CN | OC₂H₅ | green |
| 23 | 4-OC₄H₉ | 4-N(C₄H₉)₂ | CH₃ | COOC₈H₁₇ | OH/OCH₃ | grey-blue |
| 24 | 2-Cl | 4-N(CH₃)₂<br>2-CH₃<br>5-OCH₃ | CH₂—C₆H₅ | COOC₈H₁₇ | OC₂H₅/OH | dark green |
| 25 | 4-OCH₃ | 2-N(CH₃)₂<br>4-N(CH₃)₂<br>5-CH₃ | C₄H₉ | CN | OC₄H₉/OH | black-grey |
| 26 | 4-OC₂H₅ | 4-N morpholine | CH₃ | CO—C₄H₉ | OH | blue-violet |
| 27 | 4-N(C₂H₅)₂ | 4-N—C₂H₅<br>\|<br>CH₂—C₆H₅<br>2-CH₃ | CH₃ | CN | OC₂H₅ | dark blue |
| 28 | 3-Cl<br>4-OCH₃ | 4-N—C₆H₅<br>\|<br>CH₃ | CH₃ | COOC₂H₅ | OC₂H₅/OH | dark green |
| 29 | 4-OC₂H₅ | 4-N(CH₃)-C₆H₄-OC₂H₅ | CH₃ | CN | OC₈H₁₇ | grey-blue |
| 30 | 4-N(C₂H₅)- phenyl | H-N(C₂H₅)-phenyl | C₂H₅ | COOC₄H₉ | OC₂H₅ | dark blue |

TABLE 2-continued

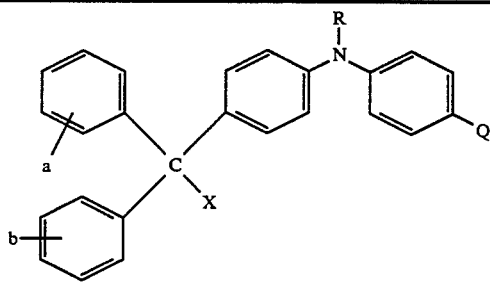

| Formula No. | a | b | R | Q | X | Colour shade on acid clay or bisphenol A |
|---|---|---|---|---|---|---|
| 31 | 4-OC$_2$H$_5$ | C$_2$H$_5$ 4-N, 3-CH(CH$_3$)C(CH$_3$)$_2$CH$_3$ | CH$_3$ | CN | OCH$_3$ | black-blue |
| 32 | 4-OCH$_3$ | 4-N(CH$_3$), 3-N(CH$_3$)— | CH$_3$ | CN | OC$_4$H$_9$ | green-black |

We claim:

1. Color-forming agents, of the formula

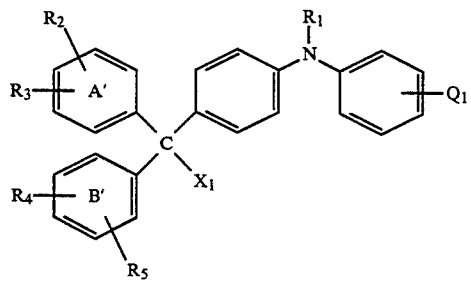

wherein $X_1$ denotes hydroxyl; $C_1$-$C_{12}$-alkoxy which is optionally substituted by chlorine or $C_1$-$C_4$-alkoxy; $C_2$-$C_{12}$-alkenyloxy; or benzyloxy or phenylethyloxy which is optionally substituted by $C_1$-$C_4$-alkyl, $C_1$-$C_4$-alkoxy or halogen, $R_1$ denotes $C_1$-$C_{12}$-alkyl or benzyl, $R_2$ and $R_4$ independently of one another denote hydrogen, chlorine, $C_1$-$C_{12}$-alkyl, $C_1$-$C_{12}$-alkoxy, phenoxy, benzyloxy or a radical of the formula

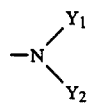

$R_3$ and $R_5$ independently of one another denote hydrogen; chlorine, $C_1$-$C_{12}$-alkyl; $C_2$-$C_{12}$-alkenyl; $C_1$-$C_{12}$-alkoxy; $C_2$-$C_{12}$-alkenyl-oxy; phenyl; benzyl; phenoxy or benzyloxy which is optionally substituted by chlorine, $C_1$-$C_{12}$-alkyl or $C_1$-$C_{14}$-alkoxy; cyclohexyloxy or cyclopentyloxy which is optionally substituted by $C_1$-$C_{12}$-alkyl; $C_1$-$C_{12}$-alkylmercapto or a radical of the formula

$Y_1$ and $Y_2$ independently of one another denote $C_1$-$C_{12}$-alkyl which is optionally substituted by chlorine, cyano, $C_1$-$C_4$-alkoxycarbonyl or $C_1$-$C_4$-alkoxy; or cyclohexyl, phenyl or benzyl, which can be substituted by chlorine, $C_1$-$C_{12}$-alkyl or $C_1$-$C_{12}$-alkoxy, or $R_2$ and $R_3$ denote members which, together with ring A' and/or $R_4$ and $R_5$ denote members which, together with ring B', are necessary to complete a ring system of the following formulae

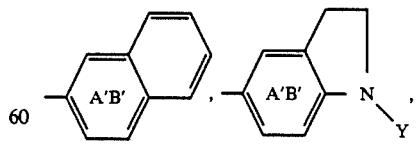

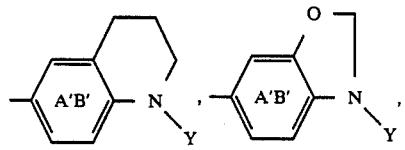

-continued

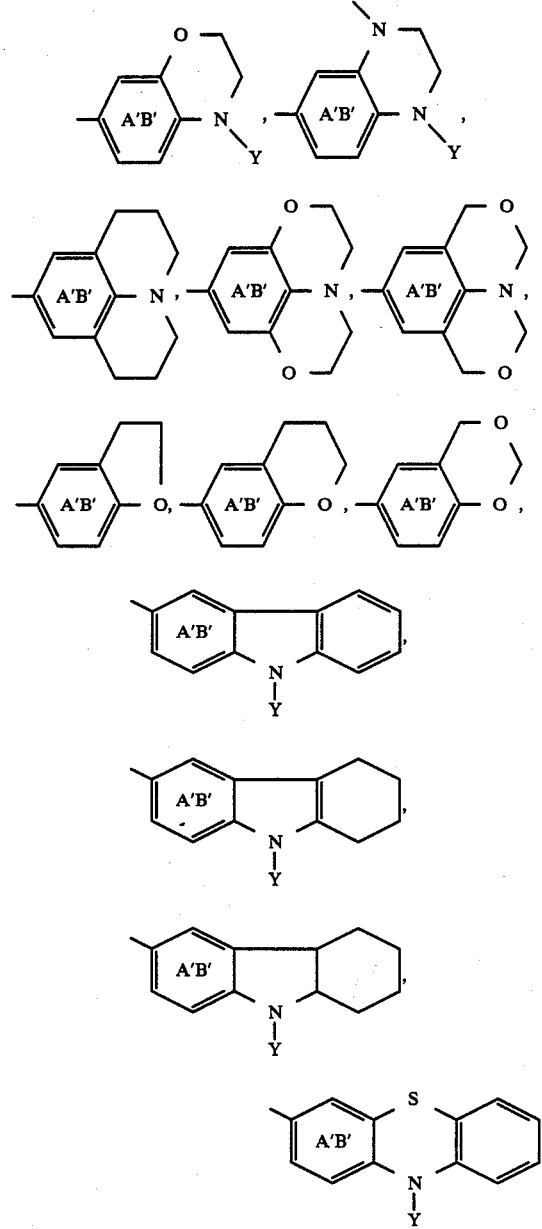

wherein
Y represents $C_1$–$C_{12}$-alkyl, which can be substituted by chlorine, cyano, $C_1$–$C_4$-alkoxycarbonyl or $C_1$–$C_4$-alkoxy; cyclohexyl, phenyl or benzyl, which can be substituted by chlorine, $C_1$–$C_{12}$-alkyl with $C_1$–$C_{12}$-alkoxy, and the saturated ring component can carry up to 4 radical from the group comprising chlorine, $C_1$- to $C_4$-alkyl, $C_1$- to $C_4$-alkoxy and phenyl, or

denotes a pyrrolo, pyrrolidino, piperidino, pipecolino, morpholino, pyrazolo or pyrazolin radical which is optionally substituted by chlorine, $C_1$- to $C_4$-alkyl or phenyl.

2. Colour-forming agents according to claim 1, of the formula

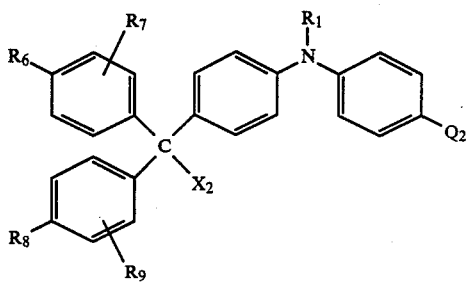

wherein
$X_2$ denotes hydroxyl or $C_1$–$C_{12}$-alkoxy,
$Q_2$ denotes cyano,
$R_6$ denotes hydrogen, chlorine, $C_1$–$C_{12}$-alkyl, $C_1$–$C_{12}$-alkoxy, benzyloxy or a radical of the formula

$R_8$ denotes $C_1$–$C_{12}$-alkoxy, benzyloxy or a radical of the formula

$R_7$ and $R_9$, independently of one another, denote hydrogen, chlorine, $C_1$–$C_{12}$-alkyl, $C_1$–$C_{12}$-alkoxy, $C_1$–$C_4$-alkylamino or di-$C_1$–$C_{12}$-alkylamino, or
$R_6$ and $R_8$ denote members which, together with the benzene ring to which they are bonded, are required to complete a ring system of the formulae

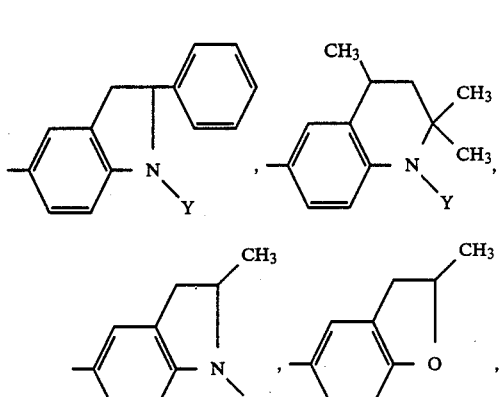

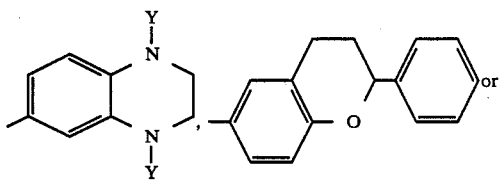

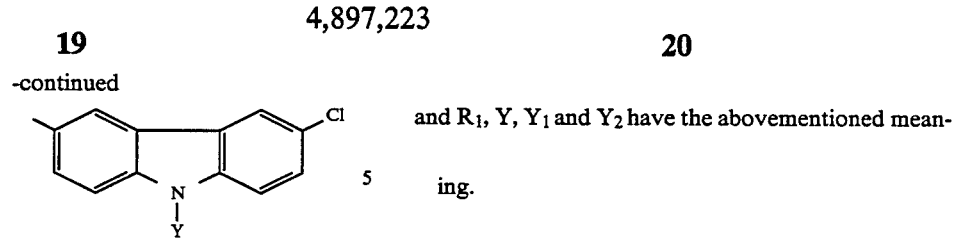
and $R_1$, $Y$, $Y_1$ and $Y_2$ have the abovementioned meaning.
* * * * *

UNITED STATES PATENT AND TRADEMARK OFFICE
CERTIFICATE OF CORRECTION

PATENT NO. : 4,897,223

DATED : January 30, 1990

INVENTOR(S) : Udo Eckstein, et al

It is certified that error appears in the above-identified patent and that said Letters Patent is hereby corrected as shown below:

Col. 15, line 52    After "halogen," insert --$Q_1$ denotes cyano,--

Col. 15, line 67    Delete "$C_{14}$" and substitute --$C_{12}$--

Signed and Sealed this

Fourth Day of February, 1992

Attest:

HARRY F. MANBECK, JR.

*Attesting Officer*    *Commissioner of Patents and Trademarks*